United States Patent
Featonby

(10) Patent No.: US 10,436,172 B2
(45) Date of Patent: Oct. 8, 2019

(54) SUBSEA APPARATUS FOR MONITORING DENSITY OR INTEGRITY OF A SUBSEA STRUCTURE OR ITS CONTENTS AND METHOD FOR GENERATING POWER ON A ROTATING PART OF A SUBSEA APPARATUS FOR MONITORING DENSITY OR INTEGRITY OF THE SUBSEA STRUCTURE OR ITS CONTENTS

(71) Applicant: JOHNSON MATTHEY PUBLIC LIMITED COMPANY, London (GB)

(72) Inventor: Paul David Featonby, Billingham (GB)

(73) Assignee: Johnson Matthey Public Limited Company, London (GB)

( * ) Notice: Subject to any disclaimer, the term of this patent is extended or adjusted under 35 U.S.C. 154(b) by 10 days.

(21) Appl. No.: 15/565,786

(22) PCT Filed: Apr. 12, 2016

(86) PCT No.: PCT/GB2016/051018
§ 371 (c)(1),
(2) Date: Oct. 11, 2017

(87) PCT Pub. No.: WO2016/166520
PCT Pub. Date: Oct. 20, 2016

(65) Prior Publication Data
US 2018/0119667 A1   May 3, 2018

(30) Foreign Application Priority Data
Apr. 13, 2015  (GB) .................................. 1506208.6

(51) Int. Cl.
*H02K 11/00* (2016.01)
*H02K 7/116* (2006.01)
(Continued)

(52) U.S. Cl.
CPC ............. *F03B 13/10* (2013.01); *H02K 5/132* (2013.01); *H02K 11/35* (2016.01);
(Continued)

(58) Field of Classification Search
None
See application file for complete search history.

(56) References Cited

U.S. PATENT DOCUMENTS 5,301,096 A * 4/1994 Klontz ................... H01F 38/14
363/37
5,594,176 A * 1/1997 Kiefer ................ G01N 29/0672
324/238

(Continued)

FOREIGN PATENT DOCUMENTS

GB   2157930 A   10/1985
GB   2496736 A   5/2013
GB   2518987 A   4/2015

OTHER PUBLICATIONS

PCT/GB2016/051018, International Search Report, dated Sep. 21, 2016.
PCT/GB2016, Written Opinion, dated Sep. 21, 2016.

*Primary Examiner* — Tulsidas C Patel
*Assistant Examiner* — S. Mikailoff
(74) *Attorney, Agent, or Firm* — BakerHostetler

(57) ABSTRACT

A subsea apparatus (1, 201) is disclosed. The subsea apparatus (1, 201) comprises a first part (2, 202) and a second part (3, 203) rotatably mounted on the first part (2, 202). The second part (3, 203) comprises electrically powered components (16). A motor (8, 208) is mounted on the first part (2, 202) and configured to drive rotation of the second part (3, 203) relative to the first part (2, 202). The apparatus also comprises a generator (12, 212) mounted on the second part (3, 203) such that rotation of the second part (3, 203) relative to the first part (2, 202) drives the generator (12, 212) to (Continued)

generate power for the electrically powered components (16). A method of providing power to a rotating part of a subsea apparatus (1, 201) is also disclosed.

9 Claims, 2 Drawing Sheets

(51) Int. Cl.
*F03B 13/10* (2006.01)
*H02K 5/132* (2006.01)
*H02K 11/35* (2016.01)
*F16H 1/06* (2006.01)
*G01N 23/06* (2018.01)

(52) U.S. Cl.
CPC ..... *F05B 2260/42* (2013.01); *F05B 2270/107* (2013.01); *F16H 1/06* (2013.01); *G01N 23/06* (2013.01); *H02K 7/116* (2013.01)

(56) References Cited

U.S. PATENT DOCUMENTS

| | | | | |
|---|---|---|---|---|
| 5,614,720 | A * | 3/1997 | Morgan | G01N 23/18 |
| | | | | 250/358.1 |
| 6,925,145 | B2 * | 8/2005 | Batzinger | G01N 23/04 |
| | | | | 378/4 |
| 7,656,997 | B1 | 2/2010 | Anjelly | |
| 9,404,773 | B2 * | 8/2016 | Chang | G21C 17/017 |
| 9,869,647 | B2 * | 1/2018 | Featonby | G01N 23/18 |
| 9,988,129 | B2 * | 6/2018 | Jamieson | B63G 8/001 |
| 10,155,569 | B2 * | 12/2018 | Kyrre | B63B 21/20 |
| 2013/0140823 | A1 * | 6/2013 | Henry | F03B 13/264 |
| | | | | 290/53 |
| 2014/0062088 | A1 * | 3/2014 | Carr | F03B 13/264 |
| | | | | 290/53 |
| 2014/0338472 | A1 * | 11/2014 | Chang | G21C 17/017 |
| | | | | 73/865.8 |
| 2016/0313263 | A1 * | 10/2016 | Featonby | G01N 23/18 |
| 2016/0318591 | A1 * | 11/2016 | Jamieson | H02J 7/025 |
| 2018/0119667 | A1 * | 5/2018 | Featonby | H02K 5/132 |

* cited by examiner

SUBSEA APPARATUS FOR MONITORING DENSITY OR INTEGRITY OF A SUBSEA STRUCTURE OR ITS CONTENTS AND METHOD FOR GENERATING POWER ON A ROTATING PART OF A SUBSEA APPARATUS FOR MONITORING DENSITY OR INTEGRITY OF THE SUBSEA STRUCTURE OR ITS CONTENTS

CROSS-REFERENCE TO RELATED APPLICATIONS

This application is the National Stage of International Patent Application No. PCT/GB2016/051018 filed Apr. 12, 2016, which claims priority from Great Britain Patent Application No. 1506208.6 filed Apr. 13, 2015, the disclosures of each of which are incorporated herein by reference in their entirety.

FIELD OF THE INVENTION

The present invention relates to a subsea apparatus and a method of generating power on a rotating part of a subsea apparatus. The apparatus and method of the invention have particular benefits for use in an undersea pipeline inspection apparatus.

BACKGROUND

In order to scan a subsea structure, such as a pipeline, it is known to mount an apparatus on the structure and then to rotate at least a part of the apparatus around the structure. An example of such an apparatus is described in GB 2496736 A. That apparatus comprises a source of gamma radiation and an array of detectors spaced apart circumferentially. The apparatus is capable of being arranged with the structure to be scanned, such as a pipeline, positioned between the source and detectors so that radiation emitted by the source can pass along the plurality of paths through a portion of the structure to the detectors. Counting the number of gamma photons transmitted from the source to the detectors, through the structure being scanned, enables differences in the density of different parts of the structure to be detected. The detectors are arranged in an arc centred on the structure to be scanned. In operation, the source and array of detectors are arranged in fixed relationship with respect to each other, and are rotated around the structure to be scanned. In this way, information about the density of the structure along a plurality of paths is obtained, enabling a high resolution density tomogram of the structure to be calculated. The apparatus can then be moved to a new position on the structure and a new scan completed.

The detectors, which are mounted on a rotating part of the apparatus, require a source of power in order to operate. It is desirable that the apparatus can be rotated continuously in one direction. Stopping the apparatus and reversing the direction of rotation takes time and may increase wear on the apparatus. Thus the source of power is desirably located on the rotating part so that no cable connections are required to the rotating part. That source of power can be a battery or other power storage device, which can be charged before deployment of the apparatus. However, a battery has limited capacity and must be recharged periodically. That has to date been done in one of two ways: the apparatus can be returned to the surface and a cable plugged into a port on the rotating part to charge the battery, or the apparatus can remain in position subsea with rotation of the apparatus halted and a Remotely Operated Vehicle (ROV) can connect a cable to a stab port on the, now stationary, rotating part and the battery can be recharged subsea via the ROV. Both of those techniques require the apparatus to cease operation, which may significantly increase the time taken to scan a lengthy structure such as a pipeline. There exists therefore a need to improve the powering of electronic devices on a rotating part of a subsea apparatus.

When conducting scans, and particularly when constructing tomograms, it is desirable to have highly accurate information about the rotational positions at which each part of the scan was completed. There is thus a need for improved systems for recording the rotational position of rotating parts of subsea apparatus.

Typically a scanning apparatus would be lowered onto the subsea structure to be scanned from above. However, during the rotating scan process parts of the apparatus may pass underneath the structure. If there were to be a failure of the drive mechanism when part of the apparatus is underneath the structure, it may not be possible to lift the apparatus off the structure. In such circumstances, it may be necessary to use an ROV to grab the rotating part of the apparatus and then attempt to rotate it using the ROV. It will be appreciated that such a manoeuvre may be challenging to perform.

In subsea applications, additional constraints arise. When operating at a depth of 1000 meter underwater, the pressure is 100 atmospheres and increases by a further 100 atmospheres for each additional 1000 meter of depth. The apparatus must be able to withstand this pressure yet remain sufficiently compact for deployment using remotely operated vehicles capable of operating at the required depth. Any increase in size of the apparatus can also result in significant increases in the force to which the apparatus is subject, since the high pressure of the water is then applied across a larger surface area.

Preferred embodiments of the present invention seek to overcome one or more of the above disadvantages of the prior art.

SUMMARY OF INVENTION

According to a first aspect of the invention there is provided a subsea apparatus comprising:
 a. A first part;
 b. A second part rotatably mounted on the first part, the second part comprising electrically powered components;
 c. A motor mounted on the first part and configured to drive rotation of the second part relative to the first part;
characterised in that, the apparatus comprises:
 d. A generator mounted on the second part such that rotation of the second part relative to the first part drives the generator to generate power for the electrically powered components.

By providing a motor on the first part that drives the rotation of the second part relative to the first part and a generator on the second part that is driven by the rotation of the second part relative to the first part, a robust way of transferring power from the first part to the second part is obtained. In particular, there is no need for cable connections between the first part and the second part, with the power transfer being instead achieved by the mechanical interactions of the motor with the second part and of the generator with the first part. It will be appreciated that such mechanical connections can be designed to be robustly operable even at subsea locations. Moreover, unlike a cable connection, such mechanical connections may place no limit on the range through which the second part can be rotated and the apparatus may then be run continuously in a single rotational direction for an extended period of time whilst continuously transferring power from the first part to the second part. Such a mechanical connection may be advantageous if the first or second part, or both parts, of the apparatus need to open and close in order to allow deployment of the apparatus. A mechanical connection may be more suitable for robust operation despite having an openable joint than an electrical connection would be.

The generator is mounted on the second part such that rotation of the second part relative to the first part drives the generator. The generator may be configured such that a drive member of the generator is engaged, directly or indirectly, by the first part such that rotation of the second part relative to the first part drives the generator. Thus the generator may be configured such that a drive member of the generator is linked to a drive mechanism that drives the drive member on rotation of the second part relative to the first part. It will be appreciated that, in order for the generator to operate, the motor must supply sufficient force to drive rotation of the second part against the resistance of the generator. The motor may therefore be supplied continuously with power from a remote location, for example a surface vessel. The power supply may comprise an electrical power supply, but preferably comprises a hydraulic power supply. That is, the motor is preferably a hydraulic motor. A power input connection, preferably a hydraulic power input connection, may be provided on the first part such that power, preferably hydraulic power, for the motor can be provided via the power input connection. The first part, which may, for example, be a frame that is mounted onto the subsea structure, may be static, in that it does not rotate, and such power supply may therefore be provided by cable or preferably hydraulic connections, for example cable or preferably hydraulic connections to a surface vessel. The apparatus may comprise control lines and other supply lines that are attached to the first part and run up to the surface to communicate with the vessel from which the apparatus is deployed. Those lines may include a power cable or preferably hydraulic line which is fixed, whether removably or otherwise, to a power input connection, preferably a hydraulic power input connection, on the first part. Thus power can be supplied to the motor mounted on the first part in an efficient way from the vessel. The lines may run via an ROV, or may run directly to the apparatus, but either way there may be the possibility of a continuous power supply from the surface to the first part.

In some embodiments, preferably embodiments in which electrical power is provided to the motor via a power input connection on the first part, the first part may comprise a power storage means, for example a battery, and the motor may draw power from the battery, which in turn draws power, either intermittently or continuously, from the power input connection. It will be understood that in such an arrangement power is still said to be provided to the motor via the power input connection since the power from the battery is derived from power provided via the power input connection. Such an arrangement may be advantageous in that, in the event of an interruption of the power supply to the input power connection, the battery may permit the apparatus to continue operating in the interval before power is restored to the power input connection.

Preferably the second part is capable of being rotated through 360° or more relative to the first part, more preferably the second part is capable of being rotated through 720° or more relative to the first part, even more preferably the second part is capable of being rotated through 1440° or more relative to the first part, yet more preferably the second part is capable of being rotated through 3600° or more relative to the first part. Advantageously the motor and generator place no upper limit on the number of 360° rotations relative to the first part through which the second part can be rotated. However, the invention may still be advantageous in apparatus which have a maximum rotation range that is 360° or less. For example, the apparatus may be configured such that it is lowered onto a structure and then the second part is rotated 180° in a first direction, then through 360° in the opposite direction and then through 180° in the first direction again such that the second part returns to its starting position. Such an arrangement may be referred to as a +/−180° scan. Whilst such a scan configuration is typically employed so as to allow the use of cable connections, the management of such cable connections may be challenging in a subsea environment, where the cables may, for example, be subject to strong currents in the sea around the apparatus and where access for re-arranging cables is limited to that which can be achieved using an ROV. The invention may therefore be advantageously deployed in such circumstances to remove the need for cable management and to increase flexibility in how the apparatus may be used.

Preferably the motor drives a toothed drive wheel, which engages with a toothed driven wheel fixedly mounted on the second part, so as to drive rotation of the second part relative to the first part. For example, the motor may have a shaft on which is mounted the drive wheel. Alternatively, the drive wheel may be connected to the motor via a gear box. Toothed wheels may be advantageous, instead of, say, belt or chain drives, in that a toothed wheel can be robustly manufactured to survive subsea conditions.

Preferably the first part comprises a toothed static wheel, fixedly mounted on the first part, and the generator comprises a toothed driver wheel engaged with the toothed static wheel such that rotation of the second part relative to the first part causes the toothed static wheel to rotate the toothed driver wheel and hence drive the generator. In that way there may be two independent sets of toothed wheels. A first set of toothed wheels, including the drive wheel and the driven wheel, are used to rotate the second part using the motor. That set has fixed wheels (in that they are fixed relative to the second part) on the second part and rotating wheels (in that they rotate relative to the first part) associated with the motor on the first part. A second set of toothed wheels, including the static wheel and the driver wheel, are used to turn the generator using the rotation of the second part. That set has fixed wheels (relative to the first part) on the first part and rotating wheels (relative to the second part) associated with the generator on the second part. It will be appreciated that the diameter and number of teeth on the various toothed wheels can be chosen so as to provide appropriate gearing ratios between the various parts of the apparatus. For example, the overall gear ratio from the rotation speed of the second part relative to the first part and the generator drive speed may be in the range of 400 to 500, preferably 425 to 475, for example 450. Thus the generator drive speed may be around 450 times the rotation speed of the second part relative to the first part.

Preferably the motor is fixedly mounted on the first part, in that it does not rotate relative to the first part. Preferably the generator is fixedly mounted on the second part, in that it does not rotate relative to the second part. The invention advantageously provides simple hydraulic or other (for example, electrical) power transfer arrangements on the first part from a power input connection, possibly via a battery or other power storage means, to the motor as a result of the fixed mounting of the motor relative to the first part and simple cabling or other power transfer arrangements on the second part from the generator to the electrically powered components, again possibly via a battery or other power storage means, as a result of the fixed mounting of the generator relative to the second part. The power transfer between the two systems is then achieved by robust rotational mechanical power transfer such as toothed wheels.

Preferably the generator comprises an ROV thruster motor configured for use as a generator. The skilled person will appreciate that a motor can be used in reverse as a generator, with the necessary modifications to the electrical connections to the motor/generator. An ROV thruster motor has the advantage that it is designed for subsea use and it may be preferable to convert an existing subsea motor to a generator rather than modify an onshore generator to make it suitable for subsea use. Preferably the generator comprises a rotational position detecting means, preferably a rotary encoder, configured to provide information relating to the position of the second part relative to the first part. That may be advantageous in that a mechanical drive system, such as toothed wheels, can be constructed with a high degree of precision and rotational position detecting means in the generator may therefore be able to provide highly accurate information about the rotational position of the second part relative to the first part. A rotary encoder may be particularly advantageous in that it may be configured to measure the rotational position of the generator shaft, which may be determined by the mechanical drive system and hence be accurately and reliably related to the rotational position of the second part. It is advantageous to provide such information on the second part, as that is where scanner detectors may be located. Moreover, since the size of the apparatus may be an important factor in determining the forces to which the apparatus is subject (since increased area of the apparatus results in the pressure of the water being applied across a larger area), combining the detection of rotational position with the electrical power provision by providing a generator comprising a rotary encoder may advantageously reduce the size of the apparatus compared to an apparatus in which those functions are performed by separate systems.

Preferably the second part comprises power storage means configured to store power generated by the generator. The power storage means may, for example, be a battery. Providing electrical power to the electrically powered components via a power storage means may be advantageous in that it permits the electrically powered components to operate for a period after the rotational motion of the second part has stopped, for example to transfer data on completion of a scan. The provision of power storage may also be advantageous in that it may permit the generator to serve as an emergency back-up motor to rotate the second part relative to the first part in the event that the motor fails. Since the apparatus will typically be lowered onto a structure with the second part in a particular position that allows that operation to occur, there is a need for a system to permit the second part to return to that position in the event the motor fails so that the apparatus can still be recovered from the structure in that event. By providing power storage means and configuring the generator such that it can be run as a motor, such a system may be provided. The generator and power storage means may only be required to provide sufficient power to rotate the second part to a position in which the apparatus can be recovered. Such a rotation may be a rotation of at most 180° for example. Thus the apparatus is preferably configured such that the generator can be operated as an emergency motor, using power from the power storage means, to rotate the second part relative to the first part if the motor fails. Preferably the apparatus includes means to disengage the motor from the second part prior to operating the generator as an emergency motor. That may be advantageous in circumstances where the motor fails in such a way as to resist rotation of the second part relative to the first part. For example, the apparatus may comprise means to move the drive wheel from a first position, in which it is engaged with the driven wheel, to a second position, in which it is disengaged from the driven wheel. The apparatus may provide clutch means for disengaging the motor from the second part.

Preferably the apparatus is an apparatus for monitoring the density or integrity of a subsea structure or the density of the contents of a subsea structure. The apparatus may be configured to record data relating to attenuation of radiation passing from a radiation source, through at least part of the subsea structure, to a detector, the source and detector being mounted on the second part. The apparatus may be configured such that power is provided by the generator to the detector in order to adjust the gain of the detector. The detector may be a scintillation detector comprising a photomultiplier tube. The detector may be a scintillation detector comprising a silicon photomultiplier.

According to a second aspect of the invention there is provided a method of generating power on a rotating part of a subsea apparatus, the method comprising:

a. Providing a subsea apparatus comprising:
    i. A first part;
    ii. A second part rotatably mounted on the first part, the second part comprising electrically powered components;
    iii. A motor mounted on the first part and configured to drive rotation of the second part relative to the first part;

characterised in that, the method comprises:
  b. Providing a generator mounted on the second part such that rotation of the second part relative to the first part drives the generator to generate power for the electrically powered components; and
  c. Operate the motor to drive rotation of the second part relative to the first part, thus operating the generator to generate power for the electrically powered components.

Thus the method uses the relative rotation of the two parts to mechanically transfer power onto the rotating part. Such a system is robust for subsea use and does not place a limit on the extent of rotation of the second part. Moreover, it advantageously confines any cabling to being either on the first part, or on the second part, and therefore there is no cabling that connects parts of the apparatus that rotate relative to each other. That means that cabling may be securely fastened to the part of the apparatus that it serves.

The method may comprise supplying power, preferably hydraulic power, to a power input connection on the first part directly from a surface vessel. The power may be supplied to the power input connection via an ROV. The power may be used to operate the motor, which is preferably a hydraulic motor. The power may be supplied directly to the motor from the power input connection or it may be supplied via power storage means, such as a battery.

Preferably the method comprises recording information relating to the position of the second part relative to the first part, the information being provided by rotational position detecting means, such as a rotary encoder, comprised in the generator. The information may be recorded on the second, rotating part of the apparatus, at least temporarily, before being transmitted to the surface or an ROV. The information may be stored in memory based on the second, rotating part of the apparatus. The information may comprise data on the angular position of the second part of the apparatus relative to the first part at which measurement data is obtained.

The method may include the step of monitoring the density of a subsea structure or the density of the contents of a subsea structure. The step may include recording data relating to attenuation of radiation passing from a radiation source, through at least part of the subsea structure, to a detector, the source and detector being mounted on the second part. The method may include the step of supplying power provided by the generator to the detector in order to adjust the gain of the detector. The detector may be a scintillation detector comprising a photomultiplier tube. The detector may be a scintillation detector comprising a silicon photomultiplier.

Preferably the method comprises storing power generated by the generator in power storage means mounted on the second part. The power storage means may, for example, be a battery. Storing power may be advantageous in that the electronic components can be powered for a time even after the apparatus has stopped rotating. That may, for example, allow for transmission of data after a measurement has completed, or status monitoring of the electronic components. Preferably sufficient power is stored to operate the electronic components for at least 10 minutes, preferably at least 30 minutes, more preferably at least an hour and even more preferably at least 3 hours after the generator has ceased operation. Advantageously, sufficient power is stored that the generator can be run for a short time as an emergency motor in the event of motor failure. Thus the method advantageously comprises operating the generator as an emergency motor, using power from the power storage means, to rotate the second part relative to the first part following a failure of the motor. It may be that the method comprises the steps of attaching the apparatus to a subsea structure with the second part in a first orientation with respect to the first part, wherein the orientation permits mounting of the apparatus on the subsea structure. For example, an opening in the first part may be aligned with an opening in the second part in the first orientation. It may be that the method comprises the step of operating the generator as an emergency motor, using power from the power storage means, to rotate the second part relative to the first part into the first orientation following a failure of the motor. The apparatus may then be removed from the subsea structure. Preferably the method comprises disengaging the motor from the second part prior to operating the generator as an emergency motor.

Preferably the method comprises rotating the detectors and the source about an angle of 360 degrees or more. That may be advantageous in that each scan position is effectively repeated, but with the source and detectors in opposite locations, at angular positions separated by 180 degrees. A 360 degree scan may therefore produce two measurements for each scan position. An advantage of the present invention is that continuous 360° scanning may be used.

Subsea locations may be locations at a depth of 100 m or greater, preferably 1000 m or greater, more preferably 3000 m or greater, yet more preferably 10000 ft (3048 m) or greater. Subsea locations may be locations at a depth in the range of 100 m to 1000 m, preferably 100 m to 3000 m, more preferably 1000 m to 3000 m or 1000 m to 10000 ft (3048 m). It will be appreciated that apparatus and methods suitable for use in deep water, for example at depths of 3000 m or 10000 ft (3048 m), may be suitable for use in shallower water, for example at depths of less than 3000 m. That may be, for example, because the hydrostatic pressure decreases with decreasing depth. However apparatus and methods suitable for use in shallow water, for example at depths of 1 m, may not be suitable for use in deeper water, for example water deeper than 1 m.

The method may be particularly advantageous in the scanning of subsea pipelines. It will be appreciated that subsea pipelines may be long structures, and that their integrity may be important to safe and environmentally responsible operation of subsea installations, but that the inspection of that integrity may be difficult to perform. The ability of the method of the invention to non-intrusively and efficiently scan significant lengths of pipeline, for example using continuous 360° scanning, may therefore be particularly advantageous.

The apparatus may be deployed using an ROV (remotely operated vehicle) at subsea locations and may be provided with clamping means to secure the apparatus to the subsea structure. The clamping means advantageously holds the first part of the apparatus in a fixed position relative to the subsea structure being scanned while a source and detectors are rotated about the subsea structure on the second part. Preferably the subsea structure is an elongate structure, for example a pipeline, having an axis, or at least a local axis for the section of the subsea structure where the apparatus is deployed, and the axis of rotation of the second part lies along the axis of the subsea structure. The scanning method may then be carried out at a plurality of circumferentially offset positions around the structure so that data may be acquired at a variety of angles through the structure. The apparatus may then be moved to a different location, preferably a different axial location, with respect to the structure and the measurement repeated. Information such as changes in density which may highlight flaws or other features within the structure can be obtained. In some embodiments the first or second part, or both parts, may be hingedly openable, for example in a clam shell arrangement wherein the part comprises a pivot and a releasable joint such that releasing the joint permits the part to swing open about the pivot. The mechanical transfer of power may be particularly advantageous in such embodiments since the elements of the mechanical transfer system, for example the toothed wheels, may be more able to operate robustly with a releasable joint in them than, for example, electrical connections.

Preferably the apparatus is provided with crawler apparatus for moving along the subsea structure. In that way the apparatus need only be deployed with an ROV at the start of the scanning process and can then be moved along the structure using the crawler apparatus provided.

Whilst the invention has been described above in relation to subsea operation and structure, it will be appreciated that aspects of the invention may also be advantageously deployed at other locations, for example onshore locations. In a third, broad aspect of the invention, there is provided an apparatus comprising:
  a. A first part;
  b. A second part rotatably mounted on the first part, the second part comprising electrically powered components;
  c. A motor mounted on the first part and configured to drive rotation of the second part relative to the first part;
characterised in that, the apparatus comprises:
  d. A generator mounted on the second part such that rotation of the second part relative to the first part drives the generator to generate power for the electrically powered components.

In a fourth, broad aspect of the invention there is provided a method of generating power on a rotating part of an apparatus, the method comprising:
  a. Providing an apparatus comprising:
    i. A first part;
    ii. A second part rotatably mounted on the first part, the second part comprising electrically powered components;
    iii. A motor mounted on the first part and configured to drive rotation of the second part relative to the first part;
characterised in that, the method comprises:
  b. Providing a generator mounted on the second part such that rotation of the second part relative to the first part drives the generator to generate power for the electrically powered components; and
  c. Operating the motor to drive rotation of the second part relative to the first part, thus operating the generator to generate power for the electrically powered components.

It will be appreciated that features described in relation to one aspect of the invention may be equally applicable in another aspect of the invention. For example, features described in relation to the methods of the invention, may be equally applicable to the apparatus of the invention, and vice versa. Some features may not be applicable to, and may be excluded from, particular aspects of the invention.

DESCRIPTION OF THE DRAWINGS

Embodiments of the present invention will now be described, by way of example, and not in any limitative sense, with reference to the accompanying drawings, of which.

DETAILED DESCRIPTION

Figure 1:
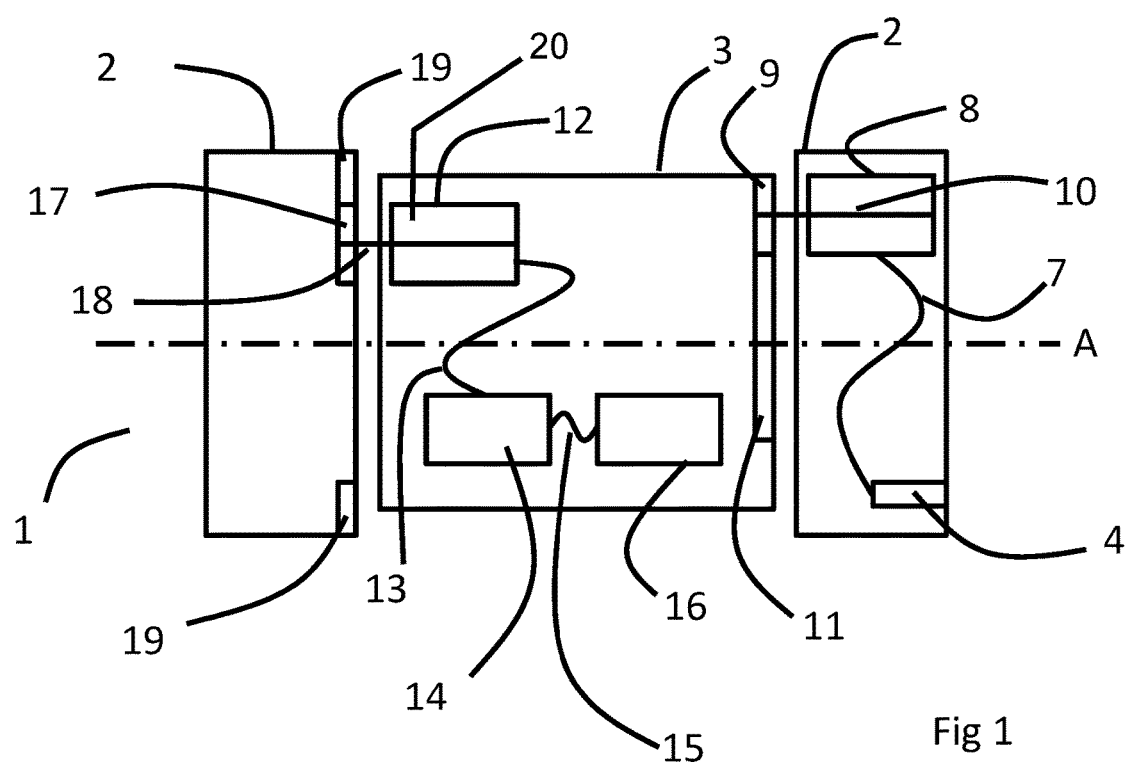
FIG. 1 is a schematic representation of a first embodiment of the invention.

In FIG. 1, an apparatus 1 comprises a first part 2 (shown in FIG. 1 in two halves, with interconnecting members removed for clarity) and a second part 3, which is mounted on the first part 2 such that the second part 3 rotates relative to the first part 2 about axis A. A hydraulic power input connection 4 is mounted on the first part 2 and connected to hydraulic motor 8 by hydraulic line 7. Hydraulic motor 8 is mounted on the first part 2 and hydraulic line 7 can therefore be secured to first part 2 to keep it secure in subsea currents. Motor 8 includes drive shaft 10, on which is mounted drive wheel 9. Drive wheel 9 engages with driven wheel 11, which is fixed to the second part 3. Also mounted on second part 3 is generator 12, which is a subsea ROV thruster (such as those provided by Submertec) configured to operate as a generator. Generator 12 includes shaft 18 on which is mounted driver wheel 17. Driver wheel 17 engages with static wheel 19, which is fixed to the first part 2. Generator 12 may also include a rotational position detecting means, such as a rotary encoder 20, that may be configured to measure the rotational position of the shaft 18. In FIG. 1, driver wheel 17 engages with the inner circumference of static wheel 19 (visible at the top and bottom of second part 2), which runs around the outer part of first part 2. Drive wheel 9, driven wheel 11, driver wheel 17 and static wheel 19 are all toothed wheels, made, for example, from stainless steel. Generator 12 is connected by cabling 13 to power storage means 14 (for example, one or more Li-ion batteries), which is in turn connected to electrically powered components 16 via cabling 15. Since generator 12, power storage means 14 and electrically powered components 16 are all mounted on second part 3, cabling 13 and cabling 15 can be secured to second part 3 to keep them in order.

In operation, hydraulic power is supplied to hydraulic power input connection 4, for example from a surface vessel. That power is used to power hydraulic motor 8. Hydraulic motor 8 turns drive wheel 9, which acts on driven wheel 11 to cause second part 3 to rotate relative to first part 2. That rotation causes static wheel 19 to act on driver wheel 17 and cause driver wheel 17 to rotate shaft 18 and thus drive generator 12. Generator 12 produces electrical power, which is used to power the electrically powered components 16 either directly or via power storage means 14. Excess power that is not used to power the electrically powered components is stored in power storage means 14 and can be used to power the electrically powered components 16 when the second part 3 is not rotating. The stored power may also be used in the event of failure of motor 8, to drive generator 12 as an emergency motor for a short period of time.

Figure 2:
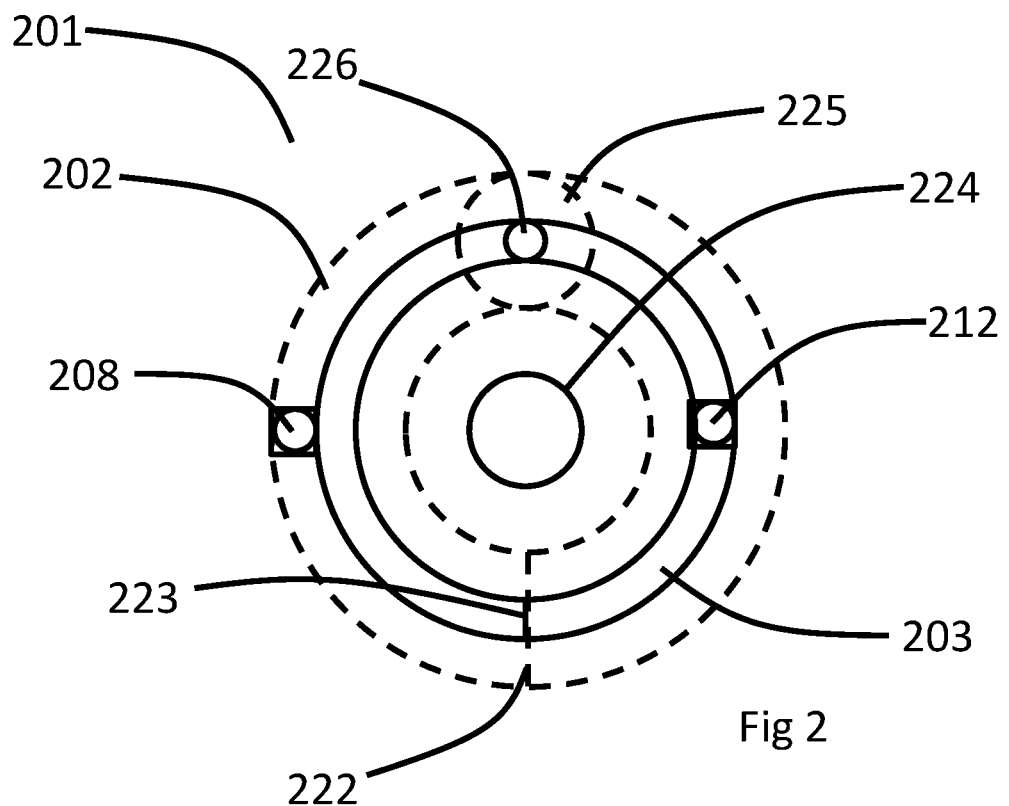
FIG. 2 is a schematic representation of a second embodiment of the invention in a first orientation.

In FIG. 2, an apparatus 201 is in a first orientation. The apparatus 201 includes first part 202 (indicated generally with dashed lines in FIG. 3) and second part 203 and is arranged in position to start scanning a subsea pipeline 224. Both first part 202 and second part 203 are clam-shell arrangements, with pivot 225 on the first part 202 and pivot 226 on the second part 203, permitting the parts to swing open so as to allow the apparatus 201 to be deployed onto the pipeline 224. The parts are fastened shut using fasteners at join 222 on first part 202 and join 223 on second part 203. Motor 208 is mounted on first part 202 and generator 212 is mounted on second part 203. In the first orientation the joins 222 and 223 are aligned so that the apparatus 201 can be opened for deployment onto the pipeline 224.

Figure 3:
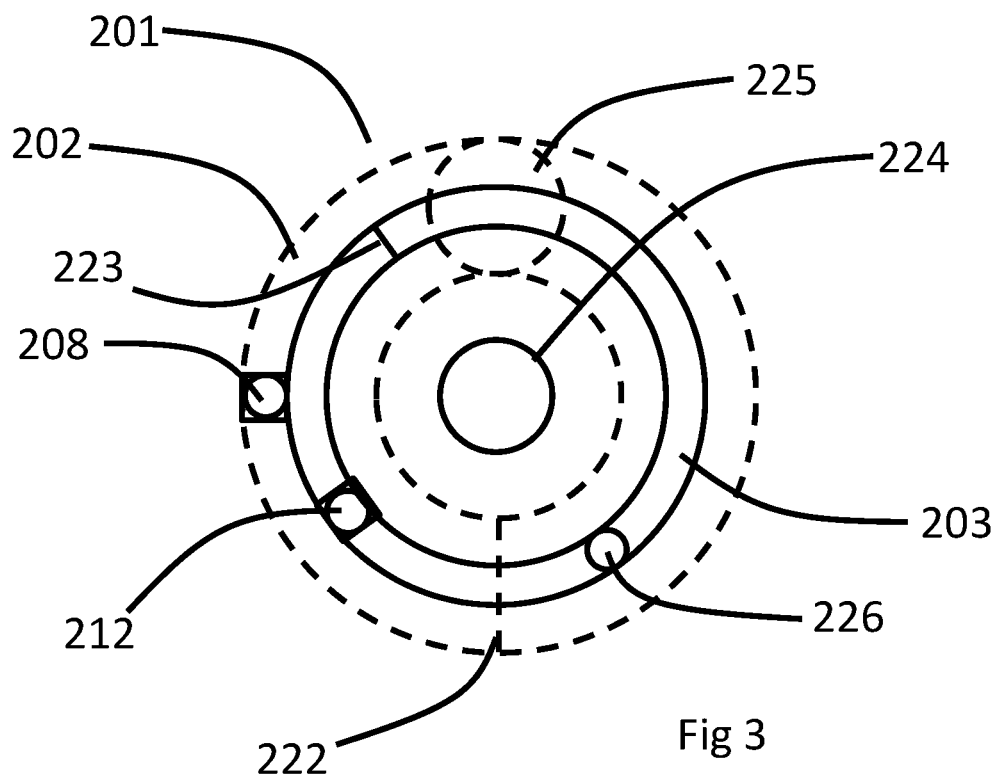
FIG. 3 is a schematic representation of the second embodiment of the invention in a second orientation.

In FIG. 3, a potential scenario is depicted in which motor 208 has failed part way through a scan of pipeline 224. Apparatus 201 is now in a second orientation in which pivots 225 and 226 and joins 222 and 223 are not aligned. Thus the clam-shell arrangements of parts 202 and 203 cannot be operated to open apparatus 201. As a result, the apparatus 201 cannot be removed from the pipeline 224 in the second orientation and instead needs to be returned to the first orientation of FIG. 2 in order for removal to take place. In such a scenario, motor 208 is disengaged from second part 203, for example by releasing a clutch mechanism and generator 212 is operated as a motor to drive second part 203 around until the first orientation is reached. At that point the joins 222 and 223 will once more be aligned and the parts 202 and 203 can be pivoted about pivots 225 and 226 respectively to open apparatus 201 and remove it from the pipeline 224.

It will be appreciated by persons skilled in the art that the above embodiments have been described by way of example only, and not in any limitative sense, and that various alterations and modifications are possible without departure from the scope of the invention as defined by the appended claims. For example, a clutch mechanism and/or a gearbox may be included in the drive train between motor 8 and driven wheel 11 in order to provide the possibility of disengaging motor 8 from driven wheel 11 or to provide an appropriate rotational velocity of second part 3. Similarly a clutch mechanism and/or gear box may be included in the drive train between static wheel 19 and generator 12. In some embodiments additional cabling may be provided to link generator 12 directly to electrically powered components 16, perhaps via a junction box. In other embodiments some supply lines may be omitted, for example if hydraulic power input connection 4 is part of hydraulic motor 8. In some embodiments power storage means 14 may be omitted completely.

The invention claimed is:

1. A subsea apparatus comprising:
 a. a first part;
 b. a second part rotatably mounted on the first part, the second part comprising electrically powered components that include a radiation source and a radiation detector;
 c. a motor mounted on the first part, the motor having a source of input power and being configured to drive rotation of the second part relative to the first part; and
 d. a generator mounted on the second part such that the rotation of the second part relative to the first part drives the generator to generate power for the electrically powered components,
 wherein the apparatus is configured to record data relating to attenuation of radiation passing from the radiation source through at least a portion of a subsea structure or of contents of the subsea structure to the radiation detector, the radiation source and radiation detector being mounted on the second part,
 wherein the motor drives a toothed drive wheel, which engages with a toothed driven wheel fixedly mounted on the second part, so as to drive the rotation of the second part relative to the first part,
 and,
 wherein the first part comprises a toothed static wheel, fixedly mounted on the first part, and the generator comprises a toothed driver wheel engaged with the toothed static wheel such that the rotation of the second part relative to the first part causes the toothed static wheel to rotate the toothed driver wheel and hence drive the generator.

2. The apparatus according to claim 1, wherein the generator comprises a rotary encoder configured to provide information relating to a position of the second part relative to the first part.

3. The apparatus according to claim 1, wherein the second part comprises power storage means configured to store power generated by the generator.

4. The apparatus according to claim 3, wherein the apparatus is configured such that the generator can be operated as an emergency motor, using power from the power storage means, to rotate the second part relative to the first part if the motor fails.

5. A method of generating power on a rotating part of a subsea apparatus for monitoring a subsea structure having a density or for monitoring contents of the subsea structure, the contents having a density, the subsea apparatus comprising:
 i. a first part;
 ii. a second part rotatably mounted on the first part, the second part comprising electrically powered components that include a radiation source and a radiation detector;
 iii. a motor mounted on the first part, the motor having a source of input power and being configured to drive rotation of the second part relative to the first part; and,
 iv. a generator mounted on the second part such that the rotation of the second part relative to the first part drives the generator to generate power for the electrically powered components, the method comprising:
  operating the motor to drive the rotation of the second part relative to the first part, thus driving the generator to generate the power for the electrically powered components, and,
  monitoring the density of the subsea structure or the density of the contents of the subsea structure by recording data relating to attenuation of radiation passing from the radiation source through at least a portion of the subsea structure or the contents of the subsea structure to the radiation detector, the radiation source and the radiation detector being mounted on the second part of the subsea apparatus,
 wherein the motor drives a toothed drive wheel, which engages with a toothed driven wheel fixedly mounted on the second part, so as to drive the rotation of the second part relative to the first part,
 and,
 wherein the first part comprises a toothed static wheel, fixedly mounted on the first part, and the generator comprises a toothed driver wheel engaged with the toothed static wheel such that the rotation of the second part relative to the first part causes the toothed static wheel to rotate the toothed driver wheel and hence drive the generator.

6. The method according to claim 5, wherein the method further comprises recording position information relating to a position of the second part relative to the first part, the position information provided by a rotary encoder comprised in the generator.

7. The method according to claim 5, wherein the method further comprises storing the power generated by the generator in power storage means mounted on the second part.

8. The method according to claim 7, wherein the method further comprises operating the generator as an emergency motor, using power from the power storage means, to rotate the second part relative to the first part following a failure of the motor.

9. The method according to claim 8, wherein the method further comprises disengaging the motor from the second part prior to operating the generator as the emergency motor.

* * * * *